United States Patent [19]

Sarma et al.

[11] Patent Number: 5,516,906
[45] Date of Patent: May 14, 1996

[54] PROCESS FOR THE PREPARATION OF N-[2-[4-(AMINOSULFONYL)PHENYL]ETHYL]5-METHYLPYRAZINECARBOXAMIDE

[75] Inventors: R. K. Sarma; P. L. Kamat, both of Bombay, Ind.

[73] Assignee: USV Limited, Bombay, Ind.

[21] Appl. No.: 375,376

[22] Filed: Jan. 17, 1995

[51] Int. Cl.⁶ ................................ C07D 241/02
[52] U.S. Cl. ................................ 544/406
[58] Field of Search ...................... 544/406

[56] References Cited

U.S. PATENT DOCUMENTS 3,669,966  6/1972  Ambrogi et al. ................ 544/406

FOREIGN PATENT DOCUMENTS 2012138  6/1969  Germany.

OTHER PUBLICATIONS

March, Advanced Org. Chemistry, 3rd Edition, pp. 348, 375, 445 and 475.
Chem. Abst. 88:190894 (1974).
Chem. Abst. 104:50893 (1985).
Chem. Abst 107:217210 (1987).
Chem. Abst 122:81407 (1994).
Miller, Ellis et al. 62 J. Am. Chem. Soc. 2099–2103 (1950).
Ambrogi, V. 2 Arz. Forsch issue 21 (1971) 200–208 (Parts I and II).

*Primary Examiner*—Cecilia Tsang
*Attorney, Agent, or Firm*—Cobrin Gittes & Samuel

[57] ABSTRACT

A process for the preparation of N-[2-[4-(amino-sulfonyl)phenyl]ethyl]-5-methylpyrazinecarboxamide is described which is simple and effective.

7 Claims, No Drawings

PROCESS FOR THE PREPARATION OF N-[2-[4-(AMINOSULFONYL) PHENYL] ETHYL] 5-METHYLPYRAZINECARBOXAMIDE

BACKGROUND OF THE INVENTION

This invention relates to a process for the preparation of N-[2-[4-(aminosulfonyl)phenyl]ethyl]-5-methylpyrazine carboxamide of the formula I:

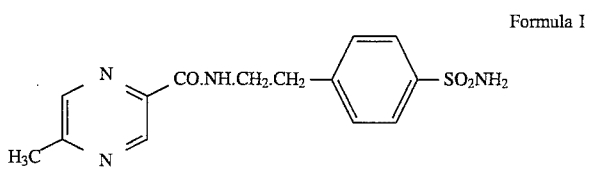

N-[2-[4-aminosulfonyl)phenyl]ethyl]-5-methylpyrazine carboxamide of the formula I is immediate or penultimate intermediate for the preparation of N-[4-(2-(5-methyl-pyrazine-2-carboxamide)-ethyl] benzene-sulphonyl]-N'cyclohexyl)-urea which is an oral antidiabetic agent. The compound of the formula I is known to be prepared by:

(a) acetylating 2-phenylethylamine of the formula II:

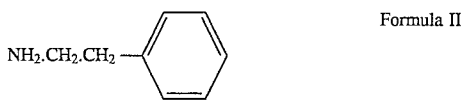

with acetic anhydride to protect the amino group and obtain N-acetyl (2-phenyl)ethylamine of the formula III:

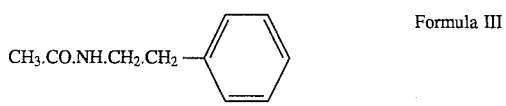

(b) chlorosulfonating the compound of the formula III with chlorosulfonic acid to obtain 4-(N-acetylamino) ethyl benzenesulfonyl chloride of the formula IV:

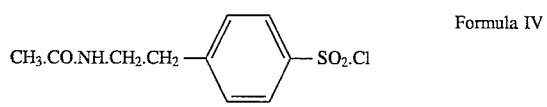

(c) treating the compound of the formula IV with ammonia to obtain 4-(2-acetylaminoethyl)benzene sulfonamide of the formula V:

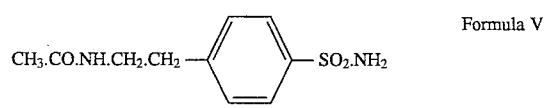

(d) hydrolysing the compound of the formula V by treating with sodium hydroxide to deprotect the amino group and obtain 4-(2-aminoethyl)benzene sulfonamide of the formula VI:

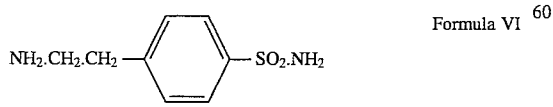

(e) treating the compound of the formula VI with hydrochloric acid to obtain 4-(2-aminoethyl)benzenesulfonamide hydrochloride of the formula VII:

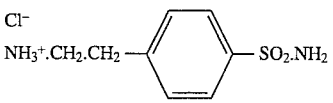

(f) purifying the compound of the formula VII by crystallization from methanol.

(g) reprecipitating the 4-(2-aminoethyl) benzene sulfonamide of the formula VI by treating the 4-(2-aminoethyl) benzene sulfonamide hydrochloride of the formula VII with sodium hydroxide; and (h) reacting the 4-(2-aminoethyl) benzenesulfonamide of the formula VI with 5-methylpyrazine-2-carboxylic acid of the formula VIII:

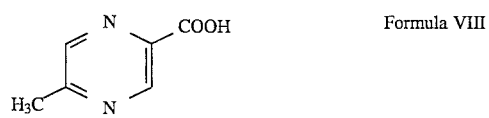

in the presence of ethyl chloroformate and triethylamine to obtain the N-[2-[4-(aminosulfonyl)phenyl] ethyl]-5 methylpyrazinecarboxamide of the formula I.

Due to protection and deprotection of the amino group in the 2-phenylethylamine the process involves a large number of steps and is lengthy and difficult to carry out. Yield of the process is low (of the order of 27%) because of the large number of steps. Ethyl chloroformate is toxic and creates pollution problem. 5-Methylpyrazine-2-carboxylic acid is difficult to be purified and pure acid is expensive.

The object of the invention is to provide a simple, easy, environment friendly and cheap process for the preparation of N-[2-[4-(aminosulfonyl)phenyl]ethyl]-5-methylpyrazine carboxamide of the formula I.

SUMMARY OF THE INVENTION

The present invention provides a process for the preparation of N-[2-[4-(aminosulfonyl)phenyl]ethyl]-5 -methylpyrazine-carboxamide of the formular I:

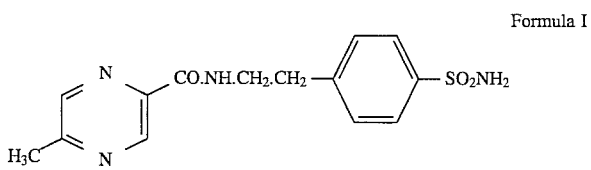

The process eleminates separate protection and deprotection of amino group in the 2-phenyl-ethylamine and is accomplished in a few simple and easy steps.

The process consists of:

i) treating 5-methylpyrazine-2-carboxylic acid of the formula VIII:

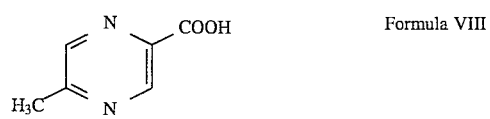

with methanol under reflux to obtain 5-methylpyrazine-2-carboxylic acid methyl ester of the formula VIII A

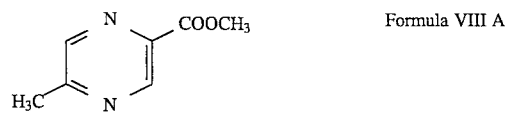

ii) reacting 5-methylpyrazine-2-carboxylic acid methyl ester of the formula VIII A with 2-phenylethylamine of the formula II:

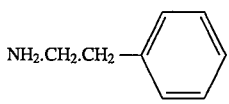

at 100° to 200° C. to obtain 5-methylpyrazine 2-(2-phenylethyl) carboxamide of the formula IX:

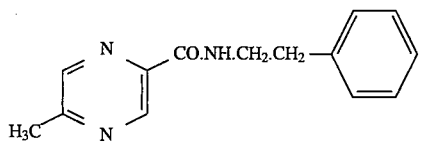

iii) chlorosulfonating the 5-methylpyrazine-2(2-phenylethyl)carboxamide of the formula IX with chlorosulfonic acid at 0°–45° C. to obtain [N-[2-[4-Chlorosulfonyl) phenyl] ethyl]-5-methylpyrazine carboxamide] of the formula X:

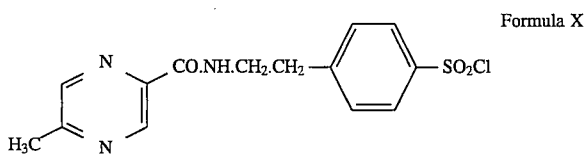

iv) and treating the (N-[2-[4-(chlorosulfonyl)phenyl] ethyl]-5-methyl pyrazine-carboxamide] of the formula X with ammonia to obtain N-[2-[4-(aminosulfonyl)phenyl]ethyl]-5 -methylpyrazine carboxamide of the formula I.

DETAILED DESCRIPTION OF THE INVENTION

According to the invention there is provided a process for the preparation of N-[2-[4-(aminosulfonyl)phenyl]ethyl] -5-methylpyrazine-carboxamide of the formula I:

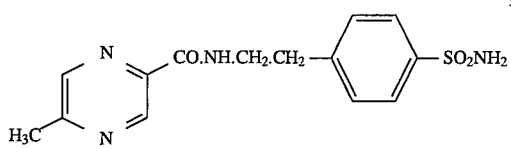

consisting of:

i) treating 5-methylpyrazine-2-carboxylic acid of the formula VIII:

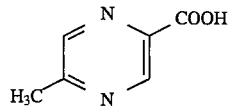

with methanol under reflux to obtain 5-methylpyrazine-2-carboxylic acid methyl ester of the formula VIII A

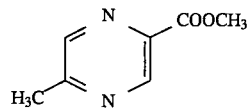

ii) reacting 5-methylpyrazine-2-carboxylic acid methyl ester of the formula VIII A with 2-phenylethylamine of the formula II:

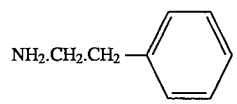

at 100° to 200° C. to obtain 5-methylpyrazine 2-(2-phenylethyl) carboxamide of the formula IX:

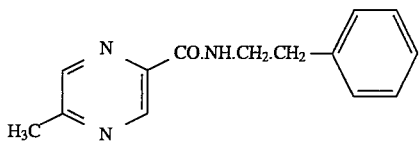

iii) chlorosulfonating the 5-methylpyrazine-2(2-phenylethyl)carboxamide of the formula IX with chlorosulfonic acid at 0°–45° C. to obtain [N-[2-[4-Chlorosulfonyl)phenyl]ethyl]-5 -methylpyrazine carboxamide] of the formula X:

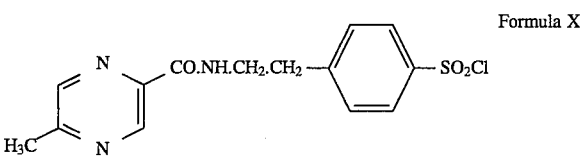

iv) and treating the (N-[2-[4-(chlorosulfonyl)phenyl] ethyl]-5-methyl pyrazine-carboxamide] of the formula X with ammonia to obtain N-[2-[4-(aminosulfonyl)phenyl]ethyl]-5-methylpyrazine carboxamide of the formula I.

According to an embodiment of the invention crude 5-methylpyrazine-2-carboxylic acid is treated with methanol in step i.

Preferably the reaction of compounds of the formulae VIIIA and II is carried out at 120°–150° C.

Preferably the compound of the formula IX is chlorosulfonated with chlorosulfonic acid at 5°–30° C.

The process of the invention eliminates separate protection and deprotection of amino group in the 2-phenylethylamine and reduces the number of steps of the process. It is, therefore, simple and easy to carry out. Yield of the process is also increased because of the reduction in the number of steps of the process. The process of the invention is environment friendly because of the elimination of ethyl chloroformate. In the process of the invention crude 5-methylpyrazine-2-carboxylic acid also may be used and it is, therefore, cheap.

The following examples are illustrative of the invention but not limitative of the scope thereof:

EXAMPLE I

5-Methylpyrazine-2-carboxylic acid crude (167 gm) was mixed with methanol (2 liters) containing con. $H_2SO_4$ (2 ml) and refluxed for 2 hours. Methanol was distilled out. The residue was extracted with water (1.5 liters) and filtered. The aqueous layer was extracted three times with 500 ml toluene each time and toluene was evaporated. The residue containing 5-methylpyrazine-2-carboxylic acid methylester (152 g) was heated at 145° C. under stirring with 2-phenylethyl amine (121 g) for 4 hours. Methanol was distilled out. The residue was dissolved in 800 ml of toluene by heating at 80° C. The solution was charcoaled and filtered. On cooling the solution to 5° C. 5-methylpyrazine (2-phenylethyl) carboxamide (225 g) was obtained and was dissolved in 900 ml of methylene chloride and added to 541.5 g of chlorosulfonic acid at 5 ° C. over a period of 2 hours. The temperature of the reaction was raised to 30° C. and held for 1 more hour. The reaction mixture was poured onto 2 kg of ice under stirring, filtered and washed with 100 ml of chilled water. The filter cake containing N-2-[4-chlorosulfonyl)phenyl] ethyl-5-methylpyrazine carboxamide was stirred with 136 g of ammonia liquor and 500 ml of water, filtered, washed free of ammonia with water and dried at 90° C. for 4 hours to obtain N-[2-[4-aminosulfonyl)phenyl]ethyl]5 -methylpyrazine carboxamide. It was recrystallized from 4 times the quantity of dioxane to obtain pure N-[2-[4-(aminosulfonyl)phenyl]ethyl]-5-methylpyrazinecarboxamide. Yield 200 g, 66%. MP 190°–200° C.

EXAMPLE 2

5-Methylpyrazine-2-carboxylic acid (140 gm) was mixed with methanol (1.55 liters) containing conc. $H_2SO_4$ (2 ml) and refluxed for 3 hours. Methanol was distilled out. The residue was extracted with water (1.5 liters) and filtered. The aqueous layer was extracted three times with 500 ml toluene each time and toluene was evaporated. The residue containing 5-methylpyrazine-2-carboxylic acid methyl ester (76 g) was heated at 130° C. under stirring with 2-phenylethylamine (60.5 g) for 8 hours. Methanol was distilled out. The residue was dissolved in 300 ml isopropanol by heating at 70° C. The solution was charcoaled and filtered. On cooling the solution to 0° C. for 4 hours, 5-methylpyrazine (2-phenylethyl) carboxamide (105 g) was obtained of which 64.5 g was dissolved in 258 ml methylene chloride and added to 145.6 g of chlorosulfonic acid at 0° C. over a period of 1 hour. The temperature of the reaction was raised to 40° C. and held for 1 more hour. The reaction mixture was poured onto 0.5 kg of ice under stirring, filtered and washed with 100 ml chilled water. The filter cake containing N-[2-[4-chlorosulfonylphenyl]ethyl]-5-methylpyrazine carboxamide was stirred with 45 gm ammonia liquor and 200 ml water, filtered, washed free of ammonia with water and dried at 90° C. for 4 hours to obtain N-[2-[4-aminosulfonyl)phenyl] ethyl]5-methylpyrazine carboxamide. It was recrystallized from 4 times the quantity of dioxane to obtain pure N-[2- [4-[aminosulfonylphenyl]ethyl]-5-methylpyrazine carboxamide. Yield 95 gms, 56%, MP 190°–200° C.

What is claimed is:

1. A process for the preparation of N-[2-[4-(aminosulfonyl)phenyl]ethyl]-5-methylpyrazine-carboxamide of the formula I:

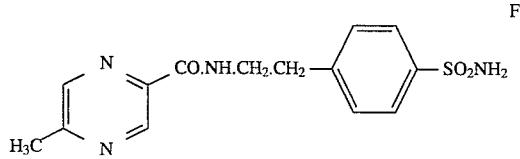

Formula I consisting of:

i) treating 5-methylpyrazine-2-carboxylic acid of the formula VIII:

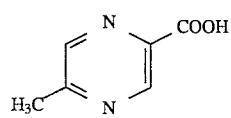

Formula VIII with methanol under reflux to obtain 5-methylpyrazine-2-carboxylic acid methyl ester of the formula VIII A:

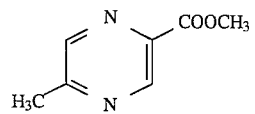

Formula VIII A ii) reacting 5-methylpyrazine-2-carboxylic acid methyl ester of the formula VIII A with 2-phenylethylamine of the formula II:

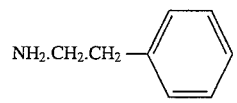

Formula II at 100° to 200° C. to obtain 5-methylpyrazine 2-(2-phenylethyl) carboxamide of the formula IX:

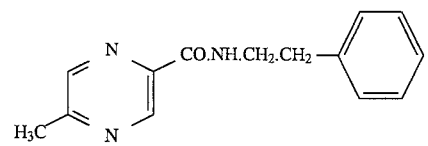

Formula IX iii) chlorosulfonating the 5-methylpyrazine-2-(2-phenylethyl)carboxamide of the formula IX with chlorosulfonic acid at 0°–45° C. to obtain [N-[2-[4-(chlorosulfonyl)phenyl]ethyl] -5-methylpyrazine carboxamide] of the formula X:

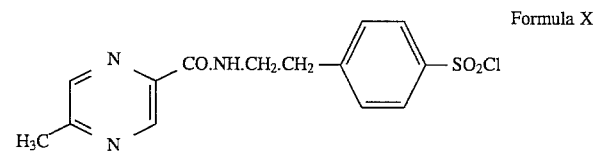

Formula X iv) and treating the [N-[2-[4-(chlorosulfonyl)phenyl] ethyl]-5-methyl purazinecarboxamide] of the formula X with ammonia to obtain N-[2-[4-(aminosulfonyl)phenyl]ethyl]-5 -methylpyrazine carboxamide of the formula I.

2. A process as claimed in claim 1, wherein the reaction of compounds of the formulae VIII A and II is carried out at 120°–150° C.

3. A process as claimed in claim 1, wherein the compound of the formula IX is chlorosulfonated with chlorosulfonic acid at 5°–40° C.

4. A process as claimed in claim 2, wherein the compound of the formula IX is chlorosulfonated with chlorosulfonic acid at 5°–40° C.

5. A process as claimed in claim 1, wherein crude 5-methylpyrazine-2-carboxylic acid is treated with methanol in step (i).

6. A process as claimed in claim 2, wherein crude 5-methylpyrazine-2-carboxylic acid is treated with methanol in step (i).

7. A process as claimed in claim 3, wherein crude 5-methylpyrazine-2-carboxylic acid is treated with methanol in step (i).

* * * * *